US008293910B2

(12) United States Patent
Sajitz et al.

(10) Patent No.: US 8,293,910 B2
(45) Date of Patent: *Oct. 23, 2012

(54) METHOD FOR PRODUCING 3,7-DIAZA-BICYCLO[3.3.1]NONANE COMPOUNDS

(75) Inventors: Melanie Sajitz, Plettenberg (DE); Steve Laborda, Hofheim (DE); Peter Naumann, Taunusstein (DE); Michael Wessling, Kandern (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 13/059,470

(22) PCT Filed: Aug. 17, 2009

(86) PCT No.: PCT/EP2009/005937
§ 371 (c)(1),
(2), (4) Date: Feb. 17, 2011

(87) PCT Pub. No.: WO2010/020383
PCT Pub. Date: Feb. 25, 2010

(65) Prior Publication Data
US 2011/0152528 A1   Jun. 23, 2011

(30) Foreign Application Priority Data

Aug. 19, 2008 (DE) .................. 10 2008 038 376

(51) Int. Cl.
C07D 471/08 (2006.01)
(52) U.S. Cl. ....................................... 546/124
(58) Field of Classification Search ................... 546/124
See application file for complete search history.

(56) References Cited

U.S. PATENT DOCUMENTS

| 3,532,634 | A | 10/1970 | Woods |
| 4,414,127 | A | 11/1983 | Fu |
| 4,626,373 | A | 12/1986 | Finch et al. |
| 6,734,155 | B1 | 5/2004 | Herbots et al. |
| 6,875,734 | B2 | 4/2005 | Reinhardt et al. |
| 7,094,745 | B2 | 8/2006 | Jonas et al. |
| 8,148,530 | B2 | 4/2012 | Wessling et al. |
| 2003/0162681 | A1 | 8/2003 | Hage et al. |
| 2009/0234124 | A1* | 9/2009 | Wessling et al. ............ 546/123 |
| 2011/0146723 | A1 | 6/2011 | Reinhardt et al. |
| 2011/0166055 | A1 | 7/2011 | Reinhardt et al. |
| 2011/0263857 | A1 | 10/2011 | Sajitz et al. |

FOREIGN PATENT DOCUMENTS

| DE | 44 43 177 | 6/1996 |
| DE | 19909546 | 6/2000 |
| DE | 102005027619 | 12/2006 |
| EP | 0 072 166 | 2/1983 |
| EP | 0 082 563 | 6/1983 |
| EP | 0 141 470 | 5/1985 |
| EP | 0 157 483 | 10/1985 |
| EP | 0 237 111 | 9/1987 |
| EP | 0765381 | 12/1995 |
| EP | 0909809 | 4/1999 |
| EP | 1 445 305 | 8/2004 |
| EP | 1 520 910 | 4/2005 |
| WO | WO 95/34628 | 12/1995 |
| WO | WO 01/45842 | 6/2001 |
| WO | WO 02/48301 A1 | 6/2002 |
| WO | WO 02/068574 A1 | 9/2002 |
| WO | WO 03/104234 A1 | 12/2003 |
| WO | WO 2005/112631 | 12/2005 |

OTHER PUBLICATIONS

International Search Report for PCT/EP2006/005582 dated Oct. 12, 2006.
Translation of International Preliminary Report on Patentability for PCT/EP2006/005582, dated Jan. 16, 2008.
International Search Report for PCT/EP2009/008907 dated Mar. 26, 2010.
Translation of International Preliminary Report on Patentability for PCT/EP2009/008907, Jun. 21, 2011.
International Search Report for PCT/EP2009/005937 dated Dec. 4, 2009.
Translation of International Preliminary Report on Patentability for PCT/EP2009/005937, dated May 12, 2011.
Borzel, Heidi, et al, "Iron coordination chemistry with tetra-, penta-andhexadentate bispidine-type ligands", Inorganica Chimica Acta, 337(2002), pp. 407-419.
Siener, Tom et al: "Synthesis and Opioid Receptor Affinity of a Series of 2,4-Diaryl- Substituted 3,7-Diazabicyclononanones", Journal of Medicinal Chemistry , 43(2000), pp. 3746-3751, Sep. 13, 2000.
Seifen-Öle-Fette-Wachse, vol. 116, No. 20/1990 on pp. 805-808.
T.H. Bennur et al., Journal of Molecular Catalysis A: Chemical 185 (2002) 71-80).
Eur. J. Org. Chem. (2008) 1019-1030.
A. Huizing et al., Mat. Res. Bull. vol. 12, pp. 605-6166, 1977.
B. Donkova et al., Thermochimica Acta, vol. 421, pp. 141-149, 2004.
International Search Report for PCT/EP2009/006163 dated Nov. 20, 2009.
Translation of International Preliminary Report on Patentability for PCT/EP2009/006163, May 26, 2011.
International Search Report for PCT/EP2009/006162 dated Nov. 10, 2009.
Translation of International Preliminary Report on Patentability for PCT/EP2009/006162, May 26, 2011.
English Abstract for DE4443177, dated Jun. 13, 1996.
English Abstract for DE19909546, dated Jun. 29, 2000.

* cited by examiner

*Primary Examiner* — Celia Chang
(74) *Attorney, Agent, or Firm* — Tod A. Waldrop

(57) ABSTRACT

The invention relates to a one-pot reaction for the production of 3,7-diaza-bicyclo[3.3.1]nonane compounds, wherein in a first step a dicarboxylic acid ester is reacted with a pyridine aldehyde and a primary amine. The piperidone created in this manner is reacted with formaldehyde and a further primary amine in a second step. It is essential to the invention that both reaction steps are carried out in a one-pot variation in a $C_1$-$C_4$ alcohol as the solvent, and that the reaction water created is removed by means of distillation.

3 Claims, No Drawings

METHOD FOR PRODUCING 3,7-DIAZA-BICYCLO[3.3.1]NONANE COMPOUNDS

The invention relates to a one-pot synthesis, i.e. an improved and simplified method for producing 3,7-diazabicyclo[3.3.1]nonane compounds without interim isolation of the piperidones, which can be carried out on an industrial scale, produces reproducibly good yields and requires a lower solvent usage.

3,7-Diazabicyclo[3.3.1]nonane compounds of the formula 1 are interesting compounds for various applications. Inter alia, they themselves or transition metal complexes which contain ligands according to formula (I) are very effective bleach catalysts

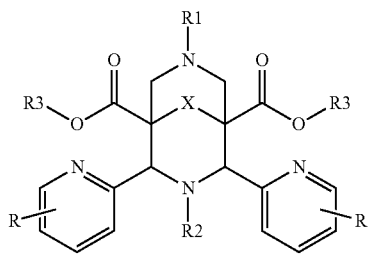

(1)

where R is hydrogen, hydroxyl, $C_1$-$C_4$-alkyl; $R^1$ is $C_1$-$C_4$-alkyl, $C_6$-$C_{1-10}$-aryl or pyridinyl-$C_1$-$C_4$-alkyl; $R^2$ is $C_1$-$C_4$-alkyl, $C_6$-$C_{1-10}$-aryl; $R^3$ is $C_1$-$C_4$-alkyl and X is C=O or C(OH)$_2$.

Their use as bleach catalyst in detergents and cleaners is claimed inter alia in WO 02/48301, US 2003/0 162 681 and WO 03/104 234.

The production of these compounds is described in Inorg. Chimica Acta, 337 (2002), 407-419 and likewise in Eur. J. Org. Chem. (2008) 1019-1030 on a laboratory scale as a two-stage method. This cannot be carried out on an industrial scale. The solvent usage is too high and the crystallization requires an excessively long time.

The production of these compounds on an industrial scale likewise takes place in two stages in accordance with the details in DE102005027619 (A1) by the following reaction scheme:

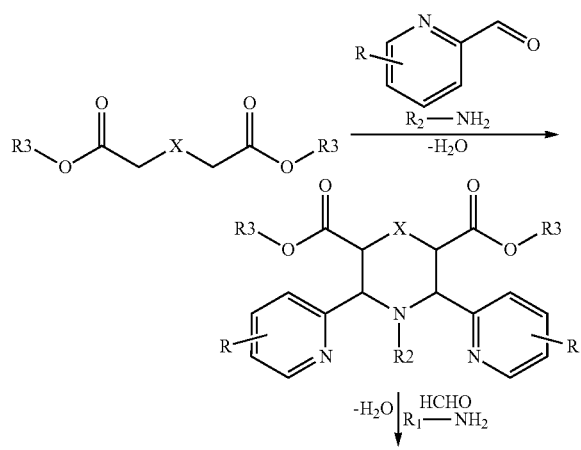

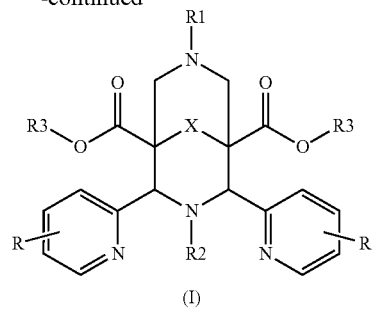

(I)

Starting from dicarboxylic acid diesters, compounds according to structural formula 1 are obtained in two Mannich condensation steps, in each case with elimination of water.

In a first reaction step, in the case of synthesis on an industrial scale, the dicarboxylic acid diester is introduced as initial charge in a $C_1$-$C_4$-alcohol, such as, for example, ethanol, propanols or butanols, preferably in a branched $C_3$- or $C_4$-alcohol and cooled to 0 to 20° C. The pyridine-2-aldehyde in question is added dropwise to the cooled mixture. The amount of aldehyde is 2.0-2.2, preferably 2.0-2.1 mole equivalents based on the diester. The temperature in this step is generally 0-20° C., preferably 5-15° C., particularly preferably 5-10° C. The metered addition takes place within 5-45 minutes, preferably within 10-20 minutes. The primary amine $R_2$—$NH_2$ is then added dropwise. The amount of amine is 0.9-1.1, preferably 0.95-1.05, mole equivalents, based on the diester. The temperature during this metered addition is generally 0-20° C., preferably 5-15° C., particularly preferably 5-10° C. The addition takes place over a period of 30-120 minutes, preferably within 60-90 minutes. When the addition is complete, the reaction mixture is heated and the content of water in the mixture is reduced under reduced pressure by azeotropic distillation. The internal temperature during the distillation is 40-60° C., preferably 45-50° C. The vacuum is adjusted accordingly. The mixture is then cooled and after-stirred, during which the temperature is 0-20° C. When the after-stirring time is complete, the product is filtered off, washed with solvent and dried.

By the two-stage method, the interim product is obtained in yields of >80%, preferably in yields of 84-88% and high purity (>95% content according to NMR).

In a second reaction step, the product from the first stage is again suspended in a $C_3$-$C_4$-alcohol, such as, for example, in propanols or butanols, preferably branched $C_3$- or $C_4$-alcohols. The alcohol in this reaction step is preferably the same alcohol as in the first reaction step. In both reaction steps, however, it is also possible to use different alcohols within the stated definition. The amine $R^1$—$NH_2$ and formalin solution are added in succession. The amount of amine is 1.2-1.6, preferably 1.4-1.5, mole equivalents, based on the interim product, the amount of formaldehyde is 3.0-4.5 mole equivalents, based on the product of the first stage. The mixture is then heated and after-stirred. The reaction time is 1-3 hours, preferably 1.5-2 hours, the temperature is 50-70° C., preferably 55-65° C. Then, under reduced pressure, the content of water in the reaction mixture is reduced as far as possible by azeotropic distillation. When distillation is complete, the mixture is firstly cooled to room temperature, then to 0-15° C., preferably to 5-10° C., and after-stirred. The product is then filtered off, washed with fresh solvent and dried.

By the two-stage method, the second stage of the formula I is obtained in yields of >50%, preferably in yields of 55-56%, in purities of >98% (content according to NMR).

The yield over two stages is 44 to 56%.

To isolate the interim product, the described synthesis method requires high solvent additions for purification and very long drying times, isolation of the solid products from the reaction apparatuses is associated with very great complexity and is thus difficult to carry out industrially. The poor pourability of the interim product is the reason for it being difficult to handle. Isolation of the interim product likewise leads to a drastic increase in the cost of the end product.

It was therefore an object to develop an improved and more cost-effective method for producing substances of the formula I which is free from the disadvantages described above. It has now been found that the compounds under discussion can also be produced by a single-stage method.

The invention provides a method for producing 3,7-diazabicyclo[3.3.1]-nonane compounds of the formula 1

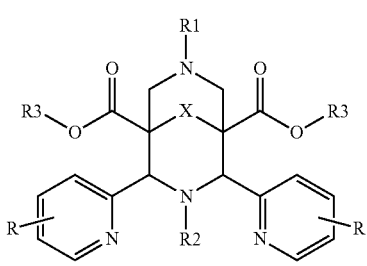

(1)

where R is hydrogen, hydroxyl, $C_1$-$C_4$-alkyl; $R^1$ is $C_1$-$C_4$-alkyl, $C_6$-$C_{10}$-aryl or pyridinyl-$C_1$-$C_4$-alkyl; $R^2$ is $C_1$-$C_4$-alkyl, $C_6$-$C_{10}$-aryl, $R^3$ is $C_1$-$C_4$-alkyl and X is C=O or C(OH)$_2$, by (a) reacting a dicarboxylic acid ester of the formula (2)

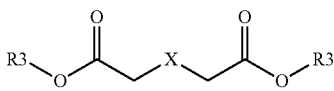

(2)

with a pyridinealdehyde of the formula (3)

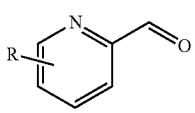

(3)

and also an amine of the formula (4)

$R^2$—$NH_2$ (4)

to give a piperidone of the formula (5)

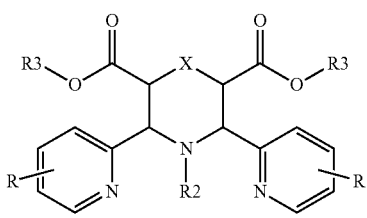

(5)

and (b) reacting the piperidones of the formula (5) obtained in this way with formaldehyde and an amine of the formula $R^1$—$NH_2$, where R, $R^1$, $R^2$ and $R^3$ have the meanings given above. This method consists in carrying out the two reaction stages in a $C_1$-$C_4$-alcohol without interim isolation of the piperidones of the formula (5) and in each case removing the water of reaction that has formed by azeotropic distillation.

The method according to the invention specifically takes place in the following way:

The dicarboxylic acid diester is introduced as initial charge in a $C_1$-$C_4$-alcohol, such as, for example, in methanol, ethanol, propanols or butanols, preferably in a branched $C_3$- or $C_4$-alcohol, and are cooled to 0-20° C. The pyridine-2-aldehyde in question is added dropwise to the cooled mixture. The amount of aldehyde is 2.0-2.2, preferably 2.0-2.1, mole equivalents, based on the diester. The temperature during this step is generally 0-20° C., preferably 5-15° C., particularly preferably 5-10° C. The metered addition takes place within 5-45 minutes, preferably within 10-20 minutes. The primary amine $R_2$—$NH_2$ is then added dropwise. The amount of amine is 0.9-1.1, preferably 0.95-1.05, mole equivalents, based on the diester. The temperature during this metered addition is generally 0-20° C., preferably 5-15° C., particularly preferably 5-10° C. The addition takes place over a period of 30-120 minutes, preferably within 60-90 minutes. When the addition is complete, the reaction mixture is heated and, under reduced pressure, the content of water in the mixture is reduced by azeotropic distillation. At least 80% of the water of reaction is removed here. At the same time, a $C_1$-$C_4$-alcohol, such as, for example, methanol, ethanol, propanols or butanols, preferably a branched $C_3$- or $C_4$-alcohol, is metered in. The alcohol in this reaction step is preferably the same alcohol as for the initial charge and is 0.8 times the amount thereof. The internal temperature during the distillation is 40-60° C., preferably 45-50° C. The vacuum is adjusted accordingly. The mixture is then cooled and after-stirred, during which the temperature is 0-20° C. The amine $R^1$—$NH_2$ and the formalin solution are then added in succession. The amount of amine is 1.2-1.6, preferably 1.4-1.5, mole equivalents, based on the intermediate product piperidone of the formula (5) (theoretical conversion of 90%). The amount of formaldehyde is 2.8-4.5, preferably 3.0, mole equivalents, based on the intermediate product of the formula (5). The mixture is then heated and after-stirred. The reaction time is 1-3 hours, preferably 1.5-2 hours, the temperature is 50-70° C., preferably 55-65° C. Then, under reduced pressure, the content of water in the reaction mixture is reduced as far as possible by azeotropic distillation. At least 80% of the water of reaction is removed here. At the same time, a fresh $C_1$-$C_4$-alcohol, such as, for example, methanol, ethanol, propanols or butanols, preferably in a branched $C_3$- or $C_4$-alcohol, is introduced. The alcohol in this reaction step is preferably the same alcohol as for the initial charge and is 2.4 times the amount thereof. When the distillation is complete, the mixture is cooled firstly to room temperature over the course of 60 minutes and after-stirred for 0.5-12 hours. The product is then filtered off, washed with solvent (a fresh $C_1$-$C_4$-alcohol, such as, for example, methanol, ethanol, propanols or butanols) and dried.

By the method according to the invention, the compound of the formula I is obtained in yields of >70%, preferably in yields of 75-80%, in a high purity (>98% content according to NMR).

The production of the compounds according to formula 1 by the method according to the invention requires, compared to the prior art, a one-pot method with a better yield instead of two reaction steps with complex and problematic isolation of the first stage a considerably reduced mass of required organic solvent. Compared to the prior art, the method can be carried out in one step without isolation of the intermediate product and therefore in a simplified manner industrially and leads to a better yield, i.e. it is considerably more cost-effective.

The method as described in the literature cannot be realized industrially from many aspects, isolation of the intermediate of the formula (5) is complex and accordingly too expensive. By introducing the one-pot method, it has been possible to solve these problems. The one-pot method guarantees more effective practicability with improved yield.

The example below is intended to illustrate the invention in more detail without limiting it thereto.

EXAMPLE 11.2 kg of dimethyl acetonedicarboxylate (97% strength; 64 mol) were dissolved in 15 kg (19 l) of isobutanol. The solution was cooled to 10° C. At this temperature, 13.4 kg of pyridine-2-aldehyde (99% strength, 125 mol) in 10 kg (13 l) of isobutanol were added dropwise and the mixture was after-stirred for 10 minutes. 4.8 kg of methylamine (40% in water, 62 mol) were then added dropwise to this mixture over the course of two hours such that the temperature could be maintained with constant cooling. The reaction mixture was warmed to room temperature over the course of 30 minutes and then heated to 40-45° C. over the course of 30 minutes.

Then, 16 kg (17 l) of isobutanol and water were distilled off under reduced pressure (initially 200-150 mbar, then 40-50 mbar) at an internal temperature of 40-45° C. in the azeotrope. During this time, 12 kg (15 l) of isobutanol were continuously metered in. The system was then aerated with nitrogen and cooled to room temperature.

8.4 kg of aminomethylpyridine (78 mol, based on the intermediate product of the formula (5) in a theoretical yield of 90%) were metered into the reaction mixture and the metering funnel was after-washed with 7.0 kg (9 l) of isobutanol. 13.5 kg of formaldehyde solution (37% in water, 166.5 mol, based on the intermediate product) were then added over the course of 15-30 minutes. When the addition was complete, the mixture was heated to 55-60° C. over the course of 30 minutes and stirred at this temperature for 1.5 hours. Then at a maximum internal temperature of 60° C. at firstly 200-150 mbar then 100-90 mbar, 55 kg (60 l) were distilled off as an azeotropic mixture of isobutanol and water. During the distillation, 36 kg (45 l) of isobutanol were continuously metered in. The system was aerated with nitrogen and cooled to room temperature over the course of one hour. After stirring for 12 h at 25° C., the precipitate was filtered off, washed three times with in each case 10 kg (13 l) of isobutanol and dried under reduced pressure at 50° C. 23.3 kg (72.1%) of 2,4-di(pyridyl)-3-methyl-7-(pyridin-2-ylmethyl)-3,7-diazabicyclo[3.3.1]nonan-9-one-1,5-dimethyldicarboxylate in the form of a colorless powder were obtained.

The invention claimed is:

1. A method for producing a 3,7-diazabicyclo[3.3.1]nonane compound of the formula 1

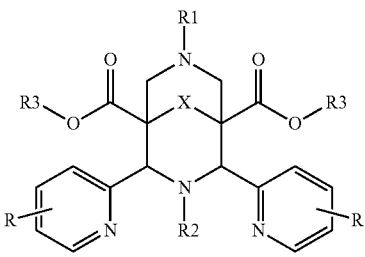

where
R is hydrogen, hydroxyl, $C_1$-$C_4$-alkyl;
$R^1$ is $C_1$-$C_4$-alkyl, $C_6$-$C_{10}$-aryl, pyridinyl-$C_1$-$C_4$-alkyl;
$R^2$ is $C_1$-$C_4$-alkyl, $C_6$-$C_{10}$-aryl;
$R^3$ is $C_1$-$C_4$-alkyl and
X is C=O or C(OH)$_2$,
comprising the steps of
(a) reacting a dicarboxylic acid ester of the formula (2)

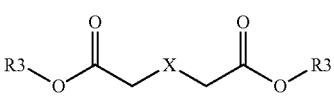

with a pyridinealdehyde of the formula (3)

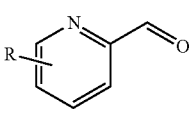

and also an amine of the formula (4)

$$R^2-NH_2 \qquad (4)$$

to give a piperidone of the formula (5)

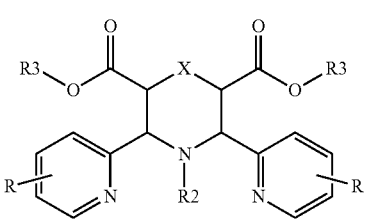

and
(b) reacting the piperidones of the formula (5) obtained in this way with formaldehyde and an amine of the formula $R^1-NH_2$, where R, $R^1$, $R^2$ and $R^3$ are defined above, wherein the reaction stages (a) and (b) are carried out in a $C_1$-$C_4$-alcohol and the water of reaction that is formed in each case is removed by azeotropic distillation, where, at the same time, a $C_1$-$C_4$-alcohol is metered in, wherein the reaction stages (a) and (b) are carried out in a one-pot method without isolation of the intermediate product (5).

2. A method as claimed in claim 1, wherein the reaction stages (a) and (b) are carried out in a branched $C_3$- or $C_4$-alcohol.

3. A method as claimed in claim 1, wherein the reaction stages (a) and (b) are carried out in isobutanol.

* * * * *